United States Patent [19]
Yoshida

[11] Patent Number: 4,943,713
[45] Date of Patent: Jul. 24, 1990

[54] BOTTLE BOTTOM INSPECTION APPARATUS

[75] Inventor: Hajime Yoshida, Tokyo, Japan

[73] Assignee: Hajime Industries Ltd., Tokyo, Japan

[21] Appl. No.: 274,929

[22] Filed: Nov. 22, 1988

[30] Foreign Application Priority Data

Nov. 27, 1987 [JP] Japan ................. 62-299417
Nov. 27, 1987 [JP] Japan ................. 62-299418

[51] Int. Cl.⁵ ............................................. G01N 21/90
[52] U.S. Cl. .................................. 250/223 B; 356/240
[58] Field of Search ............ 250/223 B; 209/524, 209/526; 356/240, 427, 428

[56] References Cited

U.S. PATENT DOCUMENTS

| | | | |
|---|---|---|---|
| 4,083,637 | 4/1978 | Ellinger et al. | 356/240 |
| 4,551,627 | 11/1985 | Reich | 250/223 B |
| 4,682,023 | 7/1987 | Yoshida | 250/223 B |
| 4,697,076 | 9/1987 | Yoshida | 250/223 B |

Primary Examiner—Edward P. Westin
Attorney, Agent, or Firm—Bauer & Schaffer

[57] ABSTRACT

A bottle bottom inspection apparatus in which an image sensor is located above a mouth of a bottle to pick up an image of the bottle bottom and the bottle bottom is irradiated upwardly by a light source and the bottle bottom is picked up by the image sensor via the bottle mouth thereby to inspect said bottle bottom. In this case, an optical device is disposed between the light source and the bottle bottom, wherein the optical device is operated to prevent the light from the light source from being directly incident on the bottle bottom but to cause the light to be incident upwardly on the bottle bottom with a predetermined incident angle from the outside of the bottle bottom.

15 Claims, 3 Drawing Sheets

BOTTLE BOTTOM INSPECTION APPARATUS

BACKGROUND OF THE INVENTION

1. Field of the Invention

The present invention relates generally to inspection apparatus and, more particularly, is directed to a bottle bottom inspection apparatus for inspecting a bottom of bottle made of a transparent material such as glass or the like.

2. Description of the Prior Art

Bottles that are made of transparent materials, such as, glass or the like for liquors, beverages, health drinks or medicines, etc., are extensively utilized up to the present time. Among such bottles, there are many cases noted where such bottles used for beer, beverage or liquors are reclaimed after reaching the final consumers, to be recycled. In such cases, the recollected bottles are reshipped after they have been sufficiently treated in the washing process and then refilled with liquids such as beer, etc., at the plant.

These recycled bottles are, however, different to the new bottles, owing to their passing through a complicated circulation that spreads over a long time period, during which time a good number of them become defective bottles that are inadequate for recycling owing to cracks at the mouth, flaws at the body or a variety of foreign matters or particles being entered into the bottles, etc.

Therefore, as a recent trend, empty bottle inspection machines have become popular, which output signals that indicate the discovery of these bottle defects by a combination of an image sensor and an electronic processor.

The items of inspection objects on such conventional empty bottle inspection machines are mainly three portions which are the bottle mouth, bottle body and bottle bottom. Accordingly, the conventional empty bottle inspection machines accomplish the inspection of the inspection objects by separate inspection apparatus that are located at different positions, respectively. Among these objects, the bottle bottom inspection is considered highly important from various reasons.

In other words, during the circulation processing after the liquid inside the bottle, such as beer, has been drunk, there are cases where cigarette butt, or such package cellophane peels, bottle caps or straws, etc. are pressed into the bottle from the bottle mouth, otherwise such foreign particles including the chips due to bottle mouth cracks enter the bottle, there are many cases that such residues are found without being completely removed from the bottle even after being wash-processed at the plants.

Moreover, such foreign particles include opaque foreign particles, or glass chips, tobacco wrapping peels or the like that are transparent foreign particles, as well as many variations of articles that have different kinds of optical characteristics to an extent that it is extremely difficult to make a bottle bottom inspection machine that is able to inspect all of these objects at the same time.

An example of the above-mentioned conventional bottle bottom inspecting apparatus that inspects a bottom of a transparent bottle will be described with reference to a schematic diagram forming FIG. 1.

As FIG. 1 shows, there is shown a bottle 1 as an example of an object to be inspected and of which the bottle bottom is represented by reference numeral 1A. An image sensor 2 which might be a video camera is located above the mouth of the bottle 1. An electronic processor 3 is adapted to process an electrical signal from the image sensor 2 to determine whether the bottle 1 is good or bad. As a light source that is used to enable the image sensor 2 to pickup a foreign particle at the bottle bottom 1A as an image, a lamp 4 and a light diffusion plate 5 of a disk-configuration made of, for example, a frosted glass are placed under the bottle bottom 1A as shown in FIG. 1. In other words, the positional relationship among the bottle 1, the image sensor 2, the lamp 4 and the light diffusion plate 5 is determined as follows. As shown in FIG. 1, the center axis of the bottle 1 is made coincident with an optical axis 0—0 of the image sensor 2, the surface of the light diffusion plate 5 is made normal to the optical axis 0—0 (substantially parallel to the bottle bottom 1A), the diameter of the light diffusion plate 5 is larger than that of the bottle bottom 1A, and the center of the light diffusion plate 5 is substantially on the optical axis 0—0. Thus, the lamp 4 irradiates the bottle bottom 1A upwardly only through the light diffusion plate 5. Accordingly, the light diffusion plate 5 functions as a planar second lighting plate (light source) for the bottle bottom 1A so that the image sensor 2 may pick up an image of the light diffusion plate 5 as a bright background (or bright field) having uniform brightness relative to the bottle bottom 1A. Thus, when on the bottle bottom 1A there is an opaque or translucent foreign particle, the image sensor 2 picks up the opaque foreign particle as a dark shade in the above bright background (or bright field). Then, on the basis of the picked-up video signal from the image sensor 2, the electronic processor 3 produces a signal indicating the existence of the opaque foreign particle on the bottle bottom 1A.

According to the conventional bottle bottom inspection apparatus as described above, if the foreign particles on the bottle bottom 1A are dark objects, opaque objects or half transparent objects, it is easy for the image sensor 2 to detect the foreign particles by picking up them as dark shades in the bright background of the bottle bottom 1A. If on the other hand the foreign particles are transparent ones such as glass chips, cellophane or the like, the light from the light diffusion plate 5 almost pass through the transparent foreign particles so that they cannot be picked up as dark shades by the image sensor 2. Even when they are picked up as shades by the image sensor 2, they are too faint to be detected by the image sensor 2.

OBJECTS AND SUMMARY OF THE INVENTION

Accordingly, it is an object of the present invention to provide an improved bottle bottom inspection apparatus which can obviate the shortcomings encountered with the prior art.

It is another object of the present invention to provide a bottle bottom inspection apparatus which can positively detect all of the foreign particles on the bottle bottom including opaque foreign particles, half transparent foreign particles as well as transparent foreign particles.

According to an aspect of the present invention, there is provided a bottle bottom inspection apparatus in which an image sensor is located above a mouth of a bottle made of a transparent material and whose bottom is to be inspected and said bottle bottom is irradiated upwardly by a light source and said bottle bottom is picked up by said image sensor via said bottle mouth thereby to inspect said bottle bottom, comprising: optical means disposed between said light source and said bottle bottom, wherein said optical means is operated to prevent a light from said light source from being directly introduced into said bottle bottom but to cause said light to be incident upwardly on said bottle bottom with a predetermined incident angle from an outside of said bottle bottom.

According to another aspect of the present invention, there is provided a bottle bottom inspection apparatus comprising:

(a) a first image sensor disposed above a mouth of a bottle to be inspected;

(b) a light diffusion plate located below a bottom of said bottle;

(c) a light source located below said light diffusion plate for irradiating upwardly said bottom of said bottle through said light diffusion plate such that said bottle bottom is picked up by said first image sensor;

(d) a first electronic processor for processing an output of said first image sensor to inspect whether an opaque or half transparent foreign particle exists on said bottle bottom;

(e) a second image sensor located above said bottle mouth at its position different from that of said first image sensor;

(f) a second electronic processor for processing an output of said second image sensor;

(g) optical means located between said bottle bottom and said light source for causing a light from said light source to be upwardly and obliquely introduced on said bottle bottom at a predetermined incident angle from the outside of said bottle bottom;

(h) light splitting means located between said first and second image sensors and said bottle mouth for splitting a light traveled through said bottle mouth from said light source to provide two separate lights;

(i) a first optical filter provided on said light diffusion plate for allowing a certain light to pass therethrough; and (j) a second optical filter located between said light splitting means and said second image sensor for preventing the light passed through said first optical filter from passing therethrough, wherein said second image sensor and said second electronic processor are operated to inspect whether a transparent foreign particle exists on said bottle bottom or not.

BRIEF DESCRIPTION OF THE DRAWINGS

A better understanding of the objects, features and advantages of the invention can be gained from a consideration of the following detailed description of the preferred embodiments thereof, in conjunction with the figures of the accompanying drawings, wherein.

DETAILED DESCRIPTION OF THE PREFERRED EMBODIMENTS

The main object of the present invention as mentioned above lies in enabling the detection of foreign particles that exist on the bottle bottom whether being opaque, half transparent or needless to say, transparent material particles.

Prior to stepping into the total explanation of the present invention, the transparent material foreign particle detection under the present invention shall be explained. Although described as transparent material, its optical characteristics are different to those of air and a part of the light incident on its surface at an angle (other than being perpendicular) shall positively be reflected thereon. In such a case, if the incident light angle is large (an incident angle smaller than the critical angle where total reflection occurs), the amount of light reflected thereon will be increased. The detection of transparent foreign particle of the present invention utilizes such above optical characteristics. To this end, while making the incident angle of the light from the light source under the bottle bottom larger (smaller than the critical angle), the incident angle is made in a variety of values, such that the light, which enters the bottle bottom, is refracted and emitted therefrom (parallel to the light incident on the bottle bottom), is incident with a certain incident angle (larger than 0 degree but smaller than the critical angle) onto any of the surfaces of the foreign particles made of transparent material, opaque material or the like reflected thereon and then reaches the image sensor.

Figure 2:
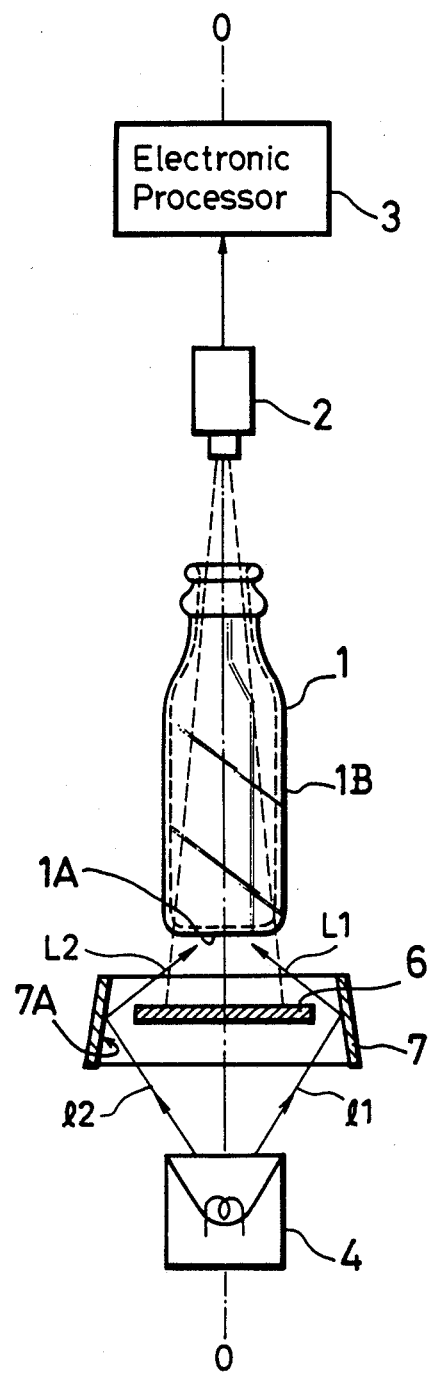
FIG. 2 is a schematic diagram showing an embodiment of a bottle bottom inspection apparatus according to the present invention.
Figure 1:
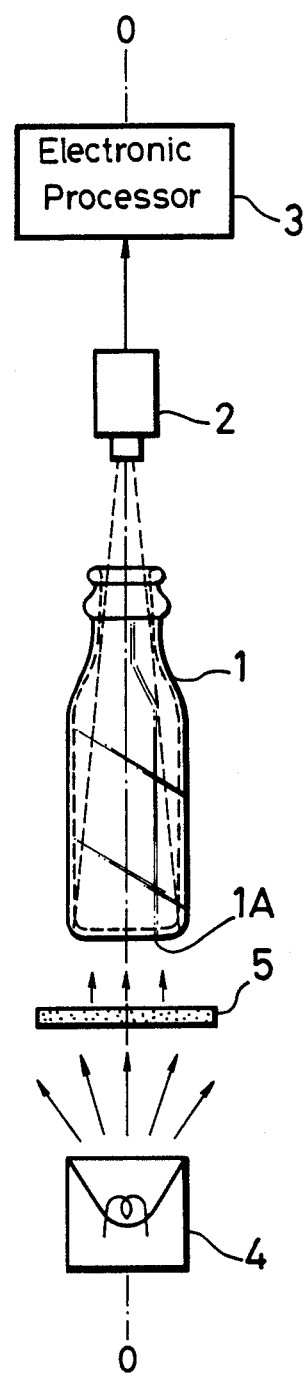
FIG. 1 is a schematic diagram showing an example of a prior art bottle bottom inspection apparatus.

An embodiment of a bottle bottom inspection apparatus according to the present invention will now be described with reference to FIG. 2. In FIG. 2, like parts corresponding to those of FIG. 1 are marked with the same references and therefore need not be described in detail.

According to this embodiment, as shown in FIG. 2, the light diffusion plate 5 used in the prior art (FIG. 1) is replaced with a circular light-shielding plate 6. The light-shielding plate 6 is made of an opaque material and the outer diameter thereof is selected to be larger than the that of the bottle bottom 1A. A cylindrical light reflection plate 7 is trapezoidal in cross section and the small inner diameter thereof is larger than the outer diameter of the light-shielding plate 6. From a position standpoint, between the bottle bottom 1A and the light source 4, the circular light-shielding plate 6 is disposed remote from the bottle bottom 1A and the light source 4 similarly to the light diffusion plate 5 and, the light reflection plate 7 disposed with its central axis substantially coincident with the optical axis 0—0 such that it encloses the outside of the light-shielding plate 6 with a predetermined spacing therebetween. As shown in FIG. 2, the light reflection mirror 7 opposes the light source 4 with its opening portion of larger diameter. Other portions are formed substantially the same as those of the example of the conventional bottle bottom inspection apparatus shown in FIG. 1.

In the embodiment of the present invention shown in FIG. 2, the light emitted from the light source 4 is not directly introduced into the bottle bottom 1A because there is provided the light-shielding plate 6 having the outer diameter larger than that of the bottle bottom 1A. Accordingly, the lights from the light source 4, which are diverged and traveled toward an inner peripheral surface (mirror surface) 7A of the light reflection mirror 7 and as typically represented by two optical paths l1 and l2 in FIG. 2, are reflected on the mirror surface 7A. Then the reflected lights are introduced into the bottle bottom 1A from the lower outer periphery of the bottle bottom 1A with an inclination, i.e., a predetermined incident angle (angle larger than 0° but smaller than the critical angle where total reflection occurs). In this case, since the outer diameter of the light-shielding plate 6 is selected to be larger than that of the bottle bottom 1A as described above, the light-shielding plate 6 becomes substantially a dark field relative to the image sensor 2 via the bottle bottom 1A contrary to the light diffusion plate 5 shown in FIG. 1. Because of the reason which will be described later, at least the surface of the light-shielding plate 6 opposing the bottle bottom 1A is preferably treated by a non-reflection process to prevent a light from being reflected as much as possible so that a undesired reflected light may not enter the bottle bottom 1A again.

Figure 3:
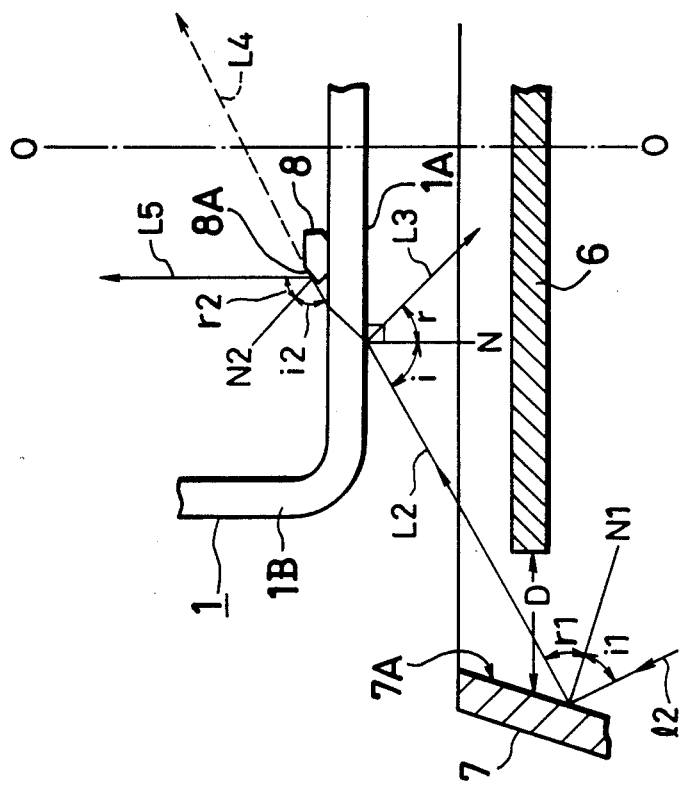
FIG. 3 is a fragmentary, enlarged view of FIG. 1.

FIG. 3 is an enlarged, fragmentary view of the bottle bottom 1A of the bottle 1, the light-shielding plate 6 and the light reflection mirror 7 of FIG. 2. The operation of the embodiment of the bottle bottom inspection apparatus according to the present invention shown in FIG. 2 will be described with reference to FIG. 3.

If now there are no foreign particles on the bottle bottom 1A, the light emitted from the light source 4 in FIG. 2 and travelling along the optical path 2 is incident on the mirror surface 7A of the light reflection mirror 7 with an incident angle i1 as shown in FIG. 3. The light reflected thereon by a reflection angle r1 travels along an optical path L2 and is incident on the under surface of the bottle bottom 1A with an incident angle i, where a part of the incident light is reflected by a reflection angle r and is advanced along an optical path L3 toward the light-shielding plate 6. The other incident light is refracted at the under surface of the bottle bottom 1A, introduced into the bottle bottom 1A, travels therethrough, and again refracted at the upper surface of the bottle bottom 1A. The light from this upper surface is traveled along an optical path L4 toward the right-angled upper portion, passed through a body portion 1B of the bottle 1 and comes outside the bottle 1. In this case, the optical paths L2 and L4 are in parallel to each other as is well known. The light traveling along the optical path L3 and reaching the upper surface of the light-shielding plate 6 is not reflected on the upper surface of the light-shielding plate 6 because the upper surface of the light-shielding plate 6 is treated by the non-reflection process as described above. Thus, the light reached to the upper surface of the light-shielding plate 6 does not travel toward the bottle bottom 1A substantially.

In the present invention, as shown in FIG. 2, since the vertical cross section of the cylindrical light reflection mirror 7 is trapezoidal in which its upper portion is small, the mirror surface 7A thereof has a like cross section. Accordingly, the mirror surface 7A is not parallel to the optical axis 0—0, in other words, the extended line of the mirror surface 7A crosses the extension of the bottle bottom 1A with an angle different from the right angle with the result that the angle i of the light incident on the bottle bottom 1A along the optical path L2 is a predetermined angle (angle larger than 0° but smaller than the critical angle). In other words, the light traveling along the optical path L2 and incident on the bottle bottom 1A from the left-angled lower portion passes through the bottle bottom 1A upward with a predetermined inclination (advances along the optical path L4) and does not reach the image sensor 2. Thus, when there are no foreign particles on the bottle bottom 1A, the image sensor 2 does not receive any light at all owing to the action of the light-shielding plate 6 and produces no output at all, so the electronic processor 3 produces no signal at all.

If on the other hand there is a foreign particle made of a transparent, opaque material or the like on the bottle bottom 1A as represented by reference numeral 8 in FIG. 3, the light traveling along the optical path L2, introduced into the bottle bottom 1A, refracted thereon and advanced along the optical path L4 remote from the upper surface of the bottle bottom 1A is reflected (at an incident angle i2 and a reflection angle r2) on a surface 8A of a part of the foreign matter 8. The thus reflected light advances upwardly along an optical path L5 which is substantially parallel to the optical axis 0—0 in FIG. 3 and introduced through the bottle mouth of the bottle 1 shown in FIG. 2 into the image sensor 2 that is located above the bottle mouth. Therefore, the image sensor 2 picks up the reflected light from the foreign particle 8 as a bright light (point of light) in the dark field, thus making it possible to detect the existence of the foreign particle 8.

In this case, light traveling through the bottle bottom 1A along other optical path parallel to the optical path L2 and incident on the surface 8A of the foreign particle 8 is reflected on the surface 8A. The reflected light therefrom is advanced along the optical path parallel to the optical path L5 and picked up by the image sensor 2. Of course, there is such a light which travels along an optical path, which is not parallel to the optical path L2, becomes incident on the surface 8A of the foreign particle 8, reflected thereon and then picked up by the image sensor 2.

The above description is chiefly given on the light traveling along the optical path l2 and incident on the mirror surface 7A. Since the mirror surface 7A is the cylindrical one of trapezoidal configuration symmetrical with respect to the optical axis 0—0 and there is an annular spacing of width D between the mirror surface 7A and the circular light-shielding plate 6, the lights emitted from the light source 4, traveling along other different optical paths and incident on the mirror surface 7A are similarly reflected thereon and become incident on the whole surface of the bottle bottom 1A at different incident angles, wherein a part of each of these lights passes the bottle bottom 1A and comes out therefrom along optical paths having different inclination angles relative to the bottle bottom 1A. Accordingly, some of them are reflected on any of the surface portions of foreign particles regardless of the place of the foreign particle and of the material of the foreign particle and advanced upward along such an optical path as the optical path L5 in FIG. 3 to reach the image sensor 2. In other words, the configurations and dimensions of the light reflection mirror 7 (its mirror surface 7A) and the light-shielding plate 6 relative to the bottle bottom 1A and the layout therebetween and their layouts relative to the bottle bottom 1A are selected in such a fashion that regardless of the position at which the foreign particle exists on the upper surface of the bottle bottom 1A, the light is reflected on any of the surfaces of foreign particle and the reflected light is reached to the image sensor 2, in other words, the light is obliquely made incident on the whole surface of the bottle bottom 1A. In FIG. 3, references N1, N and N2 respectively designate normals extended at respective reflections of the lights which travel along the optical paths L2, L2 and L4. While the surface of the foreign particle 8 is, by way of example, a mirror surface as described above, even when this surface is coarse, the amount of the reflected light traveling toward the optical path L5 is somewhat decreased, but the lights traveling along the optical paths different from the optical path L2 are also reflected on the coarse surface at the same time so that the lights traveling toward the optical path L5 are increased, thus arising no problem.

Figure 4:
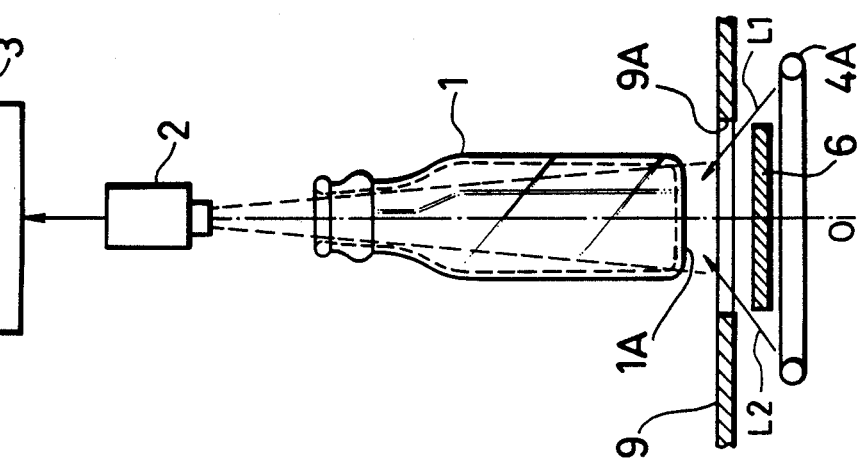
FIG. 4 is a schematic diagram showing other embodiment of a bottle bottom inspection apparatus according to the present invention.

FIG. 4 is a schematic diagram showing other embodiment of a bottle bottom inspection apparatus according to the present invention. The embodiment of FIG. 4 is different from the embodiment shown in FIGS. 2 and 3 mainly in the light source and the light-shielding means.

In the embodiment of the present invention shown in FIG. 4, an annular lamp 4A is employed as the light source. The diameter of the annular lamp 4A is larger than that of the light-shielding plate 6 similar to that in the embodiment shown in FIGS. 2 and 3. This annular lamp 4A is located below the light-shielding plate 6. In the embodiment of FIG. 4, instead of using the light reflection mirror 7 in the embodiment of FIGS. 2 and 3, a light-shielding plate 9 having a circular through-hole 9A is disposed between the light-shielding plate 6 and the bottle bottom 1A with a predetermined spacing relative to and in parallel to the light-shielding plate 6 and the bottle bottom 1A as shown in FIG. 4A. The circular through-hole 9A of the light-shielding plate 9 is slightly larger than the outer diameter of the light-shielding plate 6 and is smaller than the diameter of the annular lamp 4A. The center of the circular through-hole 9A is on the optical axis 0—0. In the embodiment of FIG. 4, since the other structure is substantially same as that of FIG. 2, like parts corresponding to those of FIG. 2 are marked with the same references and therefore need not be described in detail.

In the embodiment of FIG. 4, the diameter of the annular lamp 4 and the diameter of the circular through-hole 9A of the light-shielding plate 9 are selected in such a relationship as described above relative to both of the diameters of the bottle bottom 1A and the light-shielding plate 6. Also, the layout relations thereof are selected as described above so that owing to the actions of both of the light-shielding plates 6 and 9 and the circular through-hole 9A, the light from the circular lamp 4A is made incident on the bottle bottom 1A along optical paths similar to those along which the reflected lights from the mirror surface 7A of the light reflection mirror 7 in the embodiment of FIG. 2 travel, i.e.., typically, the optical paths L1 and L2. Therefore, the operation of the bottle bottom inspection apparatus of the embodiment in FIG. 4 is exactly the same as that of the embodiment in FIG. 2.

Figure 5:
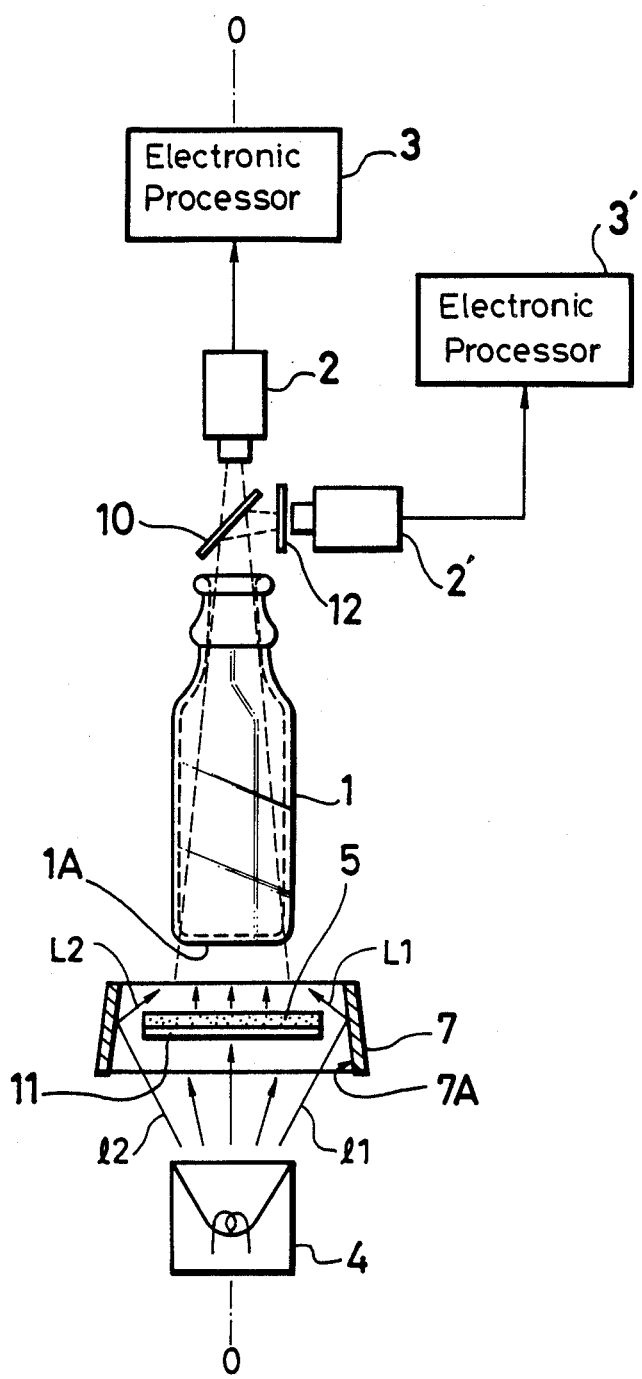
FIG. 5 is a schematic diagram showing a further embodiment of a bottle bottom inspection apparatus according to the present invention.

A further embodiment of the bottle bottom inspection apparatus according to the present invention will be described with reference to FIG. 5. The bottle bottom inspection apparatus of FIG. 5 also inspects the existence of the transparent, half transparent and translucent foreign particles on the transparent bottle bottom. In this embodiment, this type of bottle bottom inspection apparatus is formed mainly by combining the bottle bottom inspection apparatus of FIG. 2 for inspecting the transparent foreign particles and the conventional inspection apparatus of FIG. 1 for inspecting half transparent and opaque foreign particles via special optical means. Accordingly, in FIG. 5, like parts corresponding to those of FIGS. 1 and 2 are marked with the same references and need not be described in detail.

Now, a further embodiment of the bottle bottom inspection apparatus according to the present invention will be described hereinafter with reference to FIG. 5. The special optical means in this embodiment of the present invention shown in FIG. 5 comprises light splitting means, for example, a half mirror 10 disposed between the mouth of the bottle 1 and image sensors 2, 2' for splitting a light incident thereon into two separate lights, for example, lights of which the traveling directions are different from each other by 90° each, an optical filter 11 of substantially the same configuration and size as those of the light diffusion plate 5 disposed above or below (below in the illustrated embodiment) the light diffusion plate 5 for passing therethrough a light of a certain color, for example, a red light and an optical filter 12 disposed in front of one image sensor 2' for preventing a light, which passes through the optical filter 11, in this embodiment, the red light, from passing therethrough, but permitting the passage of, for example, blue light therethrough. In this case, the functions of the optical filters 11 and 12 with the different colors make the light diffusion plate 5 become a dark field relative to the image sensor 2'. On the other hand, the light diffusion plate 5 and the optical filter 11 are presented as a red bright field, in this embodiment, relative to the image sensor 2. Other arrangements are substantially the same as the main portions of the examples of FIGS. 1 and 2.

The operation of the bottle bottom inspection apparatus of the embodiment shown in FIG. 5 will be described. Referring to FIG. 5, when a part of a light (white light) from the light source, i.e., lamp 4 is passed through the optical filter 11, it becomes a monochromatic light, i.e., a red light in this embodiment. This red light is passed through the light diffusion plate 5, the bottle bottom 1A and the half mirror 10 and is introduced into the image sensor 2. On the basis of the light passing through this optical path, it is possible to inspect the foreign particle (not shown in FIG. 5) made of opaque and half transparent materials which are described in connection with FIG. 1. Specifically, if there is a foreign particle, the following advancement of the red light is disturbed by the foreign particle so that the image sensor 2 detects this foreign particle as a dark shade in the red bright field. In that case, a part of the red light passing through the mouth of the bottle 1 is reflected by the half mirror 10 and advanced toward the image sensor 2' that is used to detect the transparent foreign particle. However, because the optical filter 12 which prevents the passage of the red light therethrough is provided in front of the image sensor 2', the above-mentioned red light is absorbed by the optical filter 12 and does not reach the image sensor 2'. In other words, the image sensor 2' does not contribute at all for inspecting the opaque and half transparent foreign particles.

On the other hand, a part of the light (white light) from the lamp 4 travels toward the mirror surface 7A of the light reflection mirror 7 located outside the light diffusion plate 5 (see optical paths L1 and L2) and reflected thereon. Then the reflected light is introduced into the bottle bottom 1A from the outside in the lower side (see optical paths L1 and L2). The light traveling along the optical paths L1 and L2 advances through the optical paths exactly the same as those described in connection with FIGS. 2 and 3. Accordingly, if there exists such a transparent foreign particle 8 as shown in FIG. 3, a part of the light reflected on the surface 8A of the foreign particle 8 is advanced upward along the optical axis 0—0, passed through the mouth of the bottle 1 and reflected by the half mirror 10. The reflected light therefrom passes through the optical filter 12 and reaches the image sensor 2'. Therefore, the transparent foreign particle is inspected by the image sensor 2' and the electronic processor 3' as described in connection with FIGS. 2 and 3. That is, the image sensor 2' detects the transparent foreign particle as a bright light in the dark field. In this case, although a part of the light passes the half mirror 10 and reaches the image sensor 2, it will be apparent that this does not contribute to the operations for inspecting the foreign particle by the image sensor 2 and the electronic processor 3 at all. In this case, the surface of the light diffusion plate 5 facing the bottle bottom 1A is made as, for example, a coarse surface so that the light incident on this coarse surface along the optical path L3 in FIG. 3 can be prevented from being reflected and again introduced onto the bottle bottom 1A as much as possible.

While in the above-mentioned description the optical filters 11 and 12 are made, by way of example, such that one optical filter 11 is arranged to pass therethrough the red light, while the other optical filter 12 is made to pass therethrough the blue light, the light passing characteristics of the respective optical filters 11 and 12 are not necessarily limited to those of the above-mentioned embodiments. It is needless to say that if the optical filter 12 does not pass the light passing through the optical filter 11, it is possible to utilize optical filters having any light passing characteristics.

Further, the optical filters 11 and 12 may be replaced with polarizing filters of which the polarizing characteristics are different. In other words, it is possible to use a polarizing filter used instead of the filter 12 which does not allow the light from the polarizing filter used instead of the optical filter 11.

As described above, according to the present invention, it is possible to positively detect the foreign particles made of the transparent material and on the bottle bottom which can be hardly inspected by the prior art bottle bottom inspecting apparatus.

According to the bottle bottom inspecting apparatus of the present invention as described above, since the apparatus for inspecting the opaque and half transparent foreign particles is combined with the transparent foreign particle inspecting apparatus via the light splitting means such as the half mirror and the optical filter such as the color filter or the polarizing filter at the same position, it becomes possible to positively detect the transparent foreign particle that cannot be detected substantially in the prior art in addition to the detection of the opaque and half transparent foreign particles.

It should be understood that the above description is presented by way of example on the preferred embodiments of the invention and it will be apparent that many modifications and variations thereof could be effected by one with ordinary skill in the art without departing from the spirit and scope of the novel concepts of the invention so that the scope of the invention should be determined only by the appended claims.

I claim as my invention:

1. A bottle bottom inspection apparatus in which an image sensor is located above a mouth of a bottle made of a transparent material and whose bottom is to be inspected and said bottle bottom is irradiated upwardly by a light source exterior of said bottle and said bottle is picked up by said image sensor via said bottle mouth thereby to inspect said bottle bottom, comprising: optical means disposed between said light source and said bottle bottom, wherein said optical prevents light from said light source from being perpendicularly introduced onto said bottle bottom and causes said light to be projected upwardly onto said bottle bottom at a predetermined incident angle from a position outside the perimeter of said bottle bottom to said bottle bottom.

2. A bottle bottom inspection apparatus as claimed in claim 1, in which said optical means is formed of a disc-shaped light-shielding plate located between said bottle bottom and said light source and a cylindrical light reflection mirror located outside said light-shielding plate so as to surround the latter.

3. A bottle bottom inspection apparatus as claimed in claim 2, in which an outer diameter of said disc-shaped light-shielding plate is selected larger than that of the bottle bottom and an inner diameter of said cylindrical reflection mirror is selected larger than the outer diameter of said disc-shaped light-shielding plate.

4. A bottle bottom inspection apparatus as claimed in claim 2, in which said cylindrical light reflection mirror is formed to have a trapezoidal configuration in its vertical cross-section.

5. A bottle bottom inspection apparatus as claimed in claim 1, in which said light source is an annular lamp having a diameter larger than the outer diameter of said bottle bottom.

6. A bottle bottom inspection apparatus as claimed in claim 5, in which said optical means comprises a disc-shaped light shielding plate having an outer diameter larger than that of said bottle bottom but smaller than the diameter of said annular light source and located between said bottle bottom and said annular light source and another light-shielding plate having a circular through-hole with a diameter slightly larger than the outer diameter of said disc-shaped light shielding plate and located between said bottle bottom and said disc-shaped light-shielding plate.

7. A bottle bottom inspection apparatus as claimed in claim 4, in which said trapezoidal cylindrical light reflection mirror is so located that its shorter diameter open end faces said bottle bottom.

8. A bottle bottom inspection apparatus as claimed in claim 2, in which a surface of said disc-shaped light-shielding plate, which faces said bottle bottom, is subjected to a non-light reflection process.

9. A bottle bottom inspection apparatus comprising: (a) a first image sensor disposed above a mouth of a bottle to be inspected; (b) a light diffusion plate located below a bottom of said bottle; (c) a light source located below said light diffusion plate for irradiating upwardly said bottom of said bottle through said light diffusion plate such that said bottle bottom is picked up by said first image sensor; (d) a first electronic processor for processing an output of said first image sensor to inspect whether an opaque or half transparent foreign particle exists on said bottle bottom; (e) a second image sensor located above said bottle mouth at its position different from that of said first image sensor; (f) a second electronic processor for processing an output of said second image sensor; (g) optical means located between said bottle bottom and said light source for causing a light from said light source to be upwardly and obliquely introduced on said bottle bottom at a predetermined incident angle from the outside of said bottle bottom; (h) light splitting means located between said first and second image sensors and said bottle mouth for splitting a light traveled through said bottle mouth from said light source to provide two separate lights; (i) a first optical filter provided on said light diffusion plate for allowing a certain light to pass therethrough; and (j) a second optical filter located between said light splitting means and said second image sensor for preventing the light passed through said first optical filter from passing therethrough, wherein said second image sensor and said second electronic processor are operated to inspect whether a transparent foreign particle exists on said bottle bottom or not.

10. A bottle bottom inspection apparatus as claimed in claim 9, in which said optical means is formed of a disc-shaped light-shielding plate located between said bottle bottom and said light source and a cylindrical light reflection mirror located outside said light-shielding plate so as to surround the latter.

11. A bottle bottom inspection apparatus as claimed in claim 10, in which an outer diameter of said disc-shaped light-shielding plate is selected larger than that of the bottle bottom and an inner diameter of said cylindrical reflection mirror is selected larger than the outer diameter of said disc-shaped light-shielding plate.

12. A bottle bottom inspection apparatus as claimed in claim 10, in which said cylindrical light reflection mirror is formed to have a trapezoidal configuration in its vertical cross-section.

13. A bottle bottom inspection apparatus as claimed in claim 12, in which said trapezoidal cylindrical light reflection mirror is so located that its shorter diameter open end faces said bottle bottom.

14. A bottle bottom inspection apparatus as claimed in claim 9, in which said first optical filter is a first polarizing filter.

15. A bottle bottom inspection apparatus as claimed in claim 14, in which said second optical filter is a second polarizing filter which blocks the passage of a light passed through said first polarizing filter.

* * * * *